United States Patent [19]

Berg et al.

[11] Patent Number: 5,772,984
[45] Date of Patent: Jun. 30, 1998

[54] METHOD OF ULTRASOUND IMAGING USING MICROBUBBLE-FORMING, SOLID X-RAY CONTRAST AGENTS

[75] Inventors: Arne Berg, Sandvika; Jo Klaveness; Per Strande, both of Oslo, all of Norway; Lars Stubberud, Södertälje, Sweden

[73] Assignee: Nycomed Imaging AS, Oslo, Norway

[21] Appl. No.: 462,398

[22] Filed: Jun. 5, 1995

Related U.S. Application Data

[62] Division of Ser. No. 170,197, filed as PCT/EP92/01477, Jul. 3, 1992, Pat. No. 5,607,661.

[30] Foreign Application Priority Data

Jul. 5, 1991 [GB] United Kingdom .................. 9114565
Jan. 9, 1992 [GB] United Kingdom .................. 9200386

[51] Int. Cl.$^6$ .................................................. A61K 49/04
[52] U.S. Cl. ........................................... 424/9.52; 424/9.5
[58] Field of Search .......................... 424/9.5, 9.4, 9.411, 424/9.51, 9.52, 9.45, 450; 128/662.02

[56] References Cited

U.S. PATENT DOCUMENTS

| | | | |
|---|---|---|---|
| 4,132,731 | 1/1979 | Klieger et al. ........................ | 424/9.45 |
| 4,192,859 | 3/1980 | Mackaness et al. ..................... | 424/9.4 |
| 4,572,203 | 2/1986 | Feinstein ................................. | 128/661 |
| 4,744,989 | 5/1988 | Payne et al. ............................ | 424/490 |
| 5,233,995 | 8/1993 | Yudelson et al. ................... | 128/662.02 |

FOREIGN PATENT DOCUMENTS

| | | | |
|---|---|---|---|
| 4065189 | 3/1990 | Australia ....................... | A61K 49/00 |
| 0052575 | 5/1982 | European Pat. Off. .......... | A61B 1/00 |

*Primary Examiner*—Gary E. Hollinden
*Assistant Examiner*—Michael G. Hartley
*Attorney, Agent, or Firm*—Bacon & Thomas

[57] ABSTRACT

Ultrasound contrast agents comprising a microbubble-generating suspension of a microparticulate X-ray contrast agent in a liquid carrier medium.

9 Claims, No Drawings

METHOD OF ULTRASOUND IMAGING USING MICROBUBBLE-FORMING, SOLID X-RAY CONTRAST AGENTS

This application is a Division of application Ser. No. 08/170,197, filed Feb. 9, 1994, a 371 of PCT/EP92/01477, filed Jul. 3, 1992, now U.S. Pat. No. 5,607,661.

This invention relates to contrast agents of use in diagnostic ultrasonic imaging.

It is well known that ultrasonic imaging comprises a potentially valuable diagnostic tool, for example in studies of the vascular system, particularly in cardiography, and of tissue microvasculature. A variety of contrast agents has been proposed to enhance the acoustic images so obtained, including suspensions of solid particles, emulsified liquid droplets, gas bubbles and encapsulated gases or liquids. It is generally accepted that low density contrast agents which are easily compressible are particularly efficient in terms of the acoustic backscatter they generate, and considerable interest has therefore been shown in the preparation of gas-containing and gas-generating systems.

Initial studies involving free gas bubbles generated in vivo by intracardiac injection of physiologically acceptable substances have demonstrated the potential efficiency of such bubbles as contrast agents in echocardiography; such techniques are severely limited in practice, however, by the short lifetime of the free bubbles. Interest has accordingly been shown in methods of generating longer lived gas microbubble systems for use in echocardiography and other ultrasonic studies.

One technique which has been proposed, for example in U.S. Pat. No. 4,681,119, U.S. Pat. No. 4,442,843 and U.S. Pat. No. 1,657,756, comprises the injection of a suspension of a particulate solid (typically a saccharide such as Galactose) having a plurality of gas-filled voids and preferably also a plurality of nuclei for microbubble formation.

The present invention is based on our finding that microparticulate X-ray contrast agents may be administered in similar manner to provide substantial enhancement of contrast in ultrasound studies such as echocardiography. While we do not wish to be bound by theoretical considerations, it would appear that the particularly high density which is characteristic of conventional X-ray contrast agents serves to enhance the density differential between the generated microbubbles and their surroundings, thereby improving the echogenicity of the system.

This use of X-ray contrast agents in suspension to generate microbubble systems effective as ultrasound contrast agents may be contrasted with the previously proposed use of sonicated solutions of X-ray contrast agents such as meglumine diatrizoate as preformed microbubble systems and with previous proposals (e.g. as described in WO 90/07491) to use simple suspensions of particles of insoluble X-ray contrast agents to enhance ultrasound images by virtue of reflection of ultrasound by the particles themselves.

Thus according to one aspect of the present invention we provide X-ray contrast agents in microparticulate form adapted for administration as a microbubble-generating suspension in an appropriate liquid carrier medium (e.g. sterile, pyrogen-free water for injection, or physiologically saline), thereby acting as an ultrasound contrast agent. X-ray contrast agents may thus, for example, be presented in accordance with the invention in the form of a pack comprising an and appropriate amount of microparticulate X-ray contrast agent and advantageously also a separate volume of liquid carrier, together with instructions for preparing an intravenously administrable suspension of the microparticulate X-ray contrast agent in the carrier liquid.

According to a further embodiment of the invention there is provided a method of diagnosis in a human or animal subject by ultrasonic imaging wherein the contrast of the ultrasound image is enhanced by intravenous administration of a microbubble-generating suspension of a microparticulate X-ray contrast agent in an appropriate liquid carrier medium. A preferred method of diagnosis according to this embodiment of the invention is echocardiography.

The microparticulate X-ray contrast agents are advantageously presented in the form of aggregates, for example having an aggregate size of 20–125 micrometres, such as 30–50 micrometres, of particles having a particle size of, for example, 1–50 micrometres, such as 5–10 micrometres. Such aggregates, which may be prepared by, for example, conventional micronisation techniques such as grinding or milling, e.g. by ball-milling, will tend to contain a substantial volume of air adsorbed on their surfaces and entrained in voids such as interparticle cavities or at grain boundaries between the crystallites.

The particle size may, for example, be selected to be substantially commensurate with the desired microbubble size. In applications such as echocardiography this will typically be less than about 10 micrometres, preferably less than 7 micrometres, to permit passage through the pulmonary capillary bed and so allow enhanced ultrasound visualisation of the left side or the heart, preferably for more than one passage of circulation.

X-ray contrast agents which may be used in accordance with the invention include the wide range of known X-ray contrast agents containing iodinated phenyl groups, for example the commercially available carboxylic acid and non-ionic amide X-ray contrast agents. Such agents typically possess at least one 2,4,6-triiodophenyl group having at the 3- and/or 5-positions groups selected from carboxyl, carbamoyl, N-alkylcarbamoyl, N-hydroxyalkylcarbamoyl, acylamino, N-alkylacylamino and acylaminomethyl groupings. Alkyl groups present in such groupings may for example contain 1–6 carbon atoms; acyl groups present may for example be alkanoyl groups containing up to 6 carbon atoms. Thus representative acyl groups include acetyl, an example of an N-alkylacylamino group is N-methylacetamido, and representative N-hydroxyalkylcarbamoyl groups include N-(1,3- and 2,3-dihydroxypropyl)carbamoyl.

Examples of such X-ray contrast agents include carboxylic acids such as metrizoic acid, diatrizoic acid, iothalamic acid or ioxaglic acid and salts thereof. Non-ionic X-ray contrast agents include materials such as iohexol, iopentol, iopamidol, iodixanol, iopromide and metrizamide. Other agents include iodipamide, meglumine iodipamide, meglumine acetrizoate, meglumine diatrizoate, and acyloxyalkyl esters of carboxylic acids containing a triiodophenyl group, e.g. as described in GB-A-1363847, GB-A-2157283 and U.S. Pat. No. 4018783.

The use of water-soluble X-ray contrast agents comprises a preferred feature of the present invention. It is thought that such agents produce a longer-lasting ultrasound contrast effect since ongoing dissolution of the suspended water-soluble nicroparticulate material encourages continuing formation of microbubbles, which in turn may be stabilised by the substantially saturated solution of X-ray contrast agent in the immediate vicinity of the microbubbles tending to inhibit dissolution of the gas.

It may, however, be advantageous to modify the solubility properties of such X-ray contrast agents by physically incorporating a lipid into or onto the microparticles, in order to provide products having properties particularly suited to a specific application. There may also be advantages in modifying insoluble X-ray contrast agents in similar ways and thus according to a further feature of the invention we provide lipophile-carrying microparticulate X-ray contrast agents as a novel general class of materials.

Lipids which may be admixed with microparticulate X-ray contrast agents in accordance with the invention include fatty acids and monohydric alcohol esters thereof, fixed oils, fats, waxes, sterols, phospholipids and glycolipids. The lipid may, for example, be a high molecular weight (e.g. $C_{10-50}$) straight chain saturated or unsaturated aliphatic acid, such as capric, palmitic, stearic, linolenic, behenic, docosanedioic or melissic acid; an aralkanoic acid, e.g. a phenyl lower alkanoic acid such as 2-phenylbutyric acid; a triglyceride, for example a glyceryl ester of a high molecular weight (e.g. $C_{10-50}$) aliphatic acid, such as glyceryl trilaurate or glyceryl trimyristate; a cholanic acid such as 5β-cholanic acid; a partially hydrogenated vegetable oil such as cottonseed oil or soyabean oil; a wax, for example beeswax or carnauba wax; a high molecular weight (e.g. $C_{10-50}$) straight chain aliphatic alcohol such as stearyl alcohol or cetyl alcohol; or a mixture thereof. Mixtures of high molecular weight fatty acids such as mixtures of stearic and palmitic acids, mixtures of high molecular weight straight chain aliphatic alcohols, such as cetostearyl alcohol, mixtures of partially hydrogenated cottonseed and soyabean oils and mixtures of high molecular weight aliphatic acids and glyceryl esters such as a mixture of stearic acid and glyceryl trilaurate may, for example, be used.

Where it is desired to apply the lipid as a coating this may be effected by, for example, slurrying the microparticulate X-ray contrast agent in a solution of the lipid in an organic solvent in which the X-ray contrast agent is substantially insoluble and thereafter removing the solvent, e.g. by conventional means.

Alternatively the lipid ray be physically admixed with or within the microparticulate X-ray contrast agent, using any convenient method.

In one preferred method according to the invention, which leads to the lipid being admixed within the microparticulate structure, the X-ray contrast agent and the lipid are each dissolved in appropriate mutually miscible solvents (e.g. water in the case of water-soluble X-ray contrast agents and a lower alkanol such as ethanol in the case of lipids such as fatty acids), the resulting solutions are mixed, the solvents are removed (e.g. by evaporation under reduced pressure), and, if necessary, the resulting solid mixture is micronised (e.g. by conventional techniques such as grinding or milling, advantageously by ball-milling, to yield the desired microparticles. It will be appreciated that all such operations should be effected under sterile conditions.

In general the lipid content of contrast agents according to the invention man, for example, be in the range 0.01–5.0% w/w, advantageously 0.1–2.0% w/w, relative to the microparticulate X-ray contrast agent.

In addition to or alternatively to air, any other biocompatible gas may be employed in the contrast agents of the invention, for example nitrogen, oxygen, hydrogen, nitrous oxide, carbon dioxide, helium, argon, sulphur hexafluoride and low molecular weight optionally fluorinated hydrocarbons such as methane, acetylene or carbon tetrafluoride. The term "gas" as used herein includes any substance in the gaseous form at 37° C. The gas may be contained in the contrast agent in such a way that before use the product is non-contrast giving but becomes effective on administration, e.g. as a result of the gas forming microbubbles as a soluble X-ray contrast agent dissolves. The rate of microbubble formation may thus be controlled by, for example, selection of an appropriate degree of lipid content. In general, any gas may be introduced before, during or after any treatment such as lipid admixture with the microparticulate X-ray contrast agent.

Gas precursors useful in contrast agents according to the invention include carbonates and bicarbonates (e.g. sodium or ammonium bicarbonate) and aminomalonate esters.

For applications in echocardiography, in order to permit free passage through the pulmonary system and to achieve resonance with the preferred imaging frequency of about 0.1–15 MHz, it may be convenient to employ microbubbles and microparticles having an average size of 0.1–10 μm, e.g. 1–7 μm; the use of microparticles of average size 1–2 μm to generate microbubbles with an average size of 4–7 μm is generally advantageous. Substantially larger bubbles and particles, e.g. with average sizes of us to 500 μm, may however be useful in other applications, for example gastrointestinal imaging.

The Invention is illustrated by the following Examples:

EXAMPLE 1

METRIZAMIDE 3.75 g of freeze-dried metrizamide containing 1.2 mg sodium calcium edetate (commercially available as Amipaque, NYCOMED AS, Norway) is filled into a 20 ml vial. 3.75 g of the carrier liquid, consisting of 10 ml sterile propylene glycol mixed with 90 ml of 5% sterile dextrose solution, is then added and the resulting mixture is then shaken vigorously for 1–2 minutes. The mixture will now release gas microbubbles in the particle size range of 1–100 μm, which can be observed by light microscopy.

The mixture is to be used within 5 minutes.

EXAMPLE 2

IOHEXOL 20.0 g of iohexol (NYCOMED AS, Oslo) was ball-milled in an aluminium ball-mill with 3×1.5 cm diameter aluminium balls for 45 minutes. The resulting powder mixture consists of crystals and aggregates of iohexol. 0.75 g of the powdered mixture is then filled into a 20 ml vial. 3.0 g of the carrier liquid, which consists of 10 ml sterile propylenglycol mixed with 90 ml sterile 5% dextrose solution, is added to the vial, and vigorously shaken for about 1–2 minutes. Gas microbubbles, as observed by light microscopy, are formed. The bubble size is within the range of 1–100 μm.

The mixture is to be used within 5 minutes.

EXAMPLE 3

IODIXANOL 20.0 q of iodixanol (NYCOMED AS) was ball-milled as described in Example 2. When mixing the resulting powder with the carrier liquid described in Example 2 followed by vigorously shaking for 1–2 minutes, gas microbubbles (1–100 μm) are formed. The bubbles can be observed by light microscopy.

The mixture is to be used within 5 minutes.

EXAMPLE 4

METRIZAMIDE COATED WITH STEARIC ACID 6.75 g of metrizamide containing 2.4 mg sodium calcium edetate was ball-milled as described in Example 2. 10.6 mg stearic acid (Merck) is dissolved in 200 mg ethanol, and mixed with 5.3 g of the ball-milled powder.

3.75 g of the resulting mixture is then mixed with 3.75 ml of the carrier liquid described in Example 1 and shaken vigorously for 1–2 minutes. The mixture will now release gas microbubbles in the particle size range of 1–100 μm, which can be observed by light microscopy.

The mixture is to be used within 5 minutes.

EXAMPLE 5

METRIZAMIDE ADMIXED WITH PALMITIC ACID 10.0 g of freeze-dried metrizamide (NYCOMED AS, Oslo) were dissolved in 14.2 g of distilled water, sterile filtered and then cooled on ice to a temperature of 4°–8° C. 0.2 g of palmitic acid was dissolved in 1.2 g of 96% ethanol at 60° C. and sterile filtered. The fatty acid solution was added to the cold solution of the X-ray contrast agent under stirring, and the whole mixture was evaporated to dryness under vacuum (10 torr, 40° C.). The product was dried in a desiccator overnight. The dry substance was then ground using a stainless steel ball-mill (Retsch centrifugal ball-mill, S1) with a 50 ml grinding cup and 3×20 rim balls for 10 minutes under aseptic conditions. The-ground product was finally dried in a desiccator for 24 h before in vitro ultrasound measurements were undertaken.

EXAMPLE 6

ECHOGENICITY IN VITRO 10 ml of propylene glycol mixed with 90 ml of 5% dextrose in water was used as a carrier liquid for determining the echogenicity of products of the Examples. 1.0 g of each product to be tested was dispersed in 3.0 ml of the carrier liquid and shaken for 15 seconds. The resulting mixture as added to 52 ml of 5% human serum albumin infusion solution in the measurement cell and the acoustic effects of the products were investigated by measuring the acoustic transmission through the samples using a 5 MHz broadband transducer in a pulse-reflection technique. The temperature in the measurement cell was stabilised to 37° C. and circulation of the liquid was maintained by means of stirring at a constant rate. Ultrasound transmission through the samples was measured as a function of time over a duration of 390 seconds. Results were normalized to measurements on a reference consisting of 55 ml of 5% human serum albumin infusion solution.

The products of the Examples generally showed higher echogenicity than the reference. The product of Example 5 was characterised by substantial duration of activity as evidenced by the half life of its attenuative effect.

I claim:

1. A method of diagnosis in a human or animal subject by ultrasonic imaging wherein contrast in the ultrasound image is enhanced by intravenous administration of an ultrasound contrast agent composition comprising aggregates of microparticles of a water-soluble solid X-ray contrast agent, said aggregates forming microbubbles of biocompatible gas when suspended in a liquid carrier medium.

2. A method of diagnosis as claimed in claim 1, wherein said ultrasound contrast agent composition comprises aggregates of microparticles of a lipid and a water-soluble X-ray contrast agent.

3. A method as claimed in claim 2, wherein the aggregates have a size of 20–125 micrometers and the microparticles have a size of 1–50 micrometers.

4. A method as claimed in claim 2, wherein the aggregates have a size of 30–50 micrometers and the microparticles have a size of 5–10 micrometers.

5. A method as claimed in claim 2, wherein the lipid content is 0.01–5.0% w/w relative to the X-ray contrast agent.

6. A method as claimed in claim 2, wherein the lipid content is 0.01–2.0% w/w relative to the X-ray contrast agent.

7. A method as claimed in claim 2, wherein the lipid is a $C_{10-50}$ straight chain saturated or unsaturated aliphatic acid, a triglyceride of such an acid, or a phospholipid.

8. A method as claimed in claim 1, wherein said biocompatible gas is selected from the group consisting of air, nitrogen, oxygen, hydrogen, nitrous oxide, carbon dioxide, helium, argon, sulphurhexafluoride, low molecular weight hydrocarbons, fluorinated low molecular weight hydrocarbons, and mixtures of air with nitrogen, oxygen, hydrogen, nitrous oxide, carbon dioxide, helium, argon, sulphurhexafluoride, low molecular weight hydrocarbons, or fluorinated low molecular weight hydrocarbons.

9. A method as claimed in claim 2, wherein said biocompatible gas is selected from the group consisting of air, nitrogen, oxygen, hydrogen, nitrous oxide, carbon dioxide, helium, argon, sulphurhexafluoride, low molecular weight hydrocarbons, fluorinated low molecular weight hydrocarbons and mixtures of air with nitrogen, oxygen, hydrogen, nitrous oxide, carbon dioxide, helium, argon, sulphurhexafluoride, low molecular weight hydrocarbons, or fluorinated low molecular weight hydrocarbons.

* * * * *